United States Patent [19]

Van Gompel et al.

[11] Patent Number: 4,940,464
[45] Date of Patent: Jul. 10, 1990

[54] DISPOSABLE INCONTINENCE GARMENT OR TRAINING PANT

[75] Inventors: Paul T. Van Gompel, Hortonville; Jody D. Suprise, Neenah; Robert J. Schleinz, Appleton, all of Wis.

[73] Assignee: Kimberly-Clark Corporation, Neenah, Wis.

[21] Appl. No.: 379,026

[22] Filed: Jul. 11, 1989

Related U.S. Application Data

[63] Continuation of Ser. No. 133,674, Dec. 16, 1987, abandoned.

[51] Int. Cl.$^5$ ............................................. A61F 13/16
[52] U.S. Cl. .................................. 604/396; 604/385.2
[58] Field of Search .............................. 604/385.2, 396

[56] References Cited

U.S. PATENT DOCUMENTS

| | | |
|---|---|---|
| 2,102,359 | 12/1937 | Frieman . |
| 2,166,012 | 7/1939 | Maida . |
| 2,397,641 | 4/1946 | Blair . |
| 2,435,945 | 2/1948 | Redmond . |
| 2,538,596 | 1/1951 | Sheridan . |
| 3,087,495 | 4/1963 | Hart . |
| 3,098,484 | 7/1963 | Younger ............................ 604/396 |
| 3,142,301 | 7/1964 | Erteszek . |
| 3,368,563 | 2/1968 | Scheier ............................ 604/396 |
| 3,386,446 | 6/1968 | Sloan ................................. 2/407 |
| 3,397,696 | 8/1968 | Rickard . |
| 3,530,859 | 9/1970 | Heimowitz ........................ 604/386 |
| 3,613,687 | 10/1971 | Kennedy . |
| 3,687,141 | 8/1972 | Matsuda ............................ 604/396 |
| 3,768,481 | 10/1973 | Shibata ............................. 604/394 |
| 3,882,871 | 5/1975 | Taniguchi ......................... 604/385.2 |
| 4,031,568 | 6/1977 | Huff . |
| 4,205,679 | 6/1980 | Repke et al. . |
| 4,355,425 | 10/1982 | Jones et al. . |
| 4,425,128 | 1/1984 | Motomura . |
| 4,427,408 | 1/1984 | Karami et al. . |
| 4,522,853 | 6/1985 | Szonn et al. . |
| 4,534,769 | 8/1985 | De Jonckheere et al. ......... 604/369 |
| 4,610,680 | 9/1986 | La Fleur . |
| 4,619,649 | 10/1986 | Roberts . |
| 4,655,760 | 4/1987 | Morman et al. . |
| 4,690,681 | 9/1987 | Haunschild et al. . |
| 4,695,279 | 9/1987 | Steer . |
| 4,710,187 | 12/1987 | Boland et al. . |

FOREIGN PATENT DOCUMENTS 1520740  8/1978  United Kingdom .

Primary Examiner—C. Fred Rosenbaum
Assistant Examiner—Sharon Rose
Attorney, Agent, or Firm—Douglas L. Miller

[57] ABSTRACT

A disposable pant-like garment for absorbing human discharge is provided, and comprises an absorbent assembly comprising a liquid-impervious outer cover, a liquid-pervious liner, and an absorbent medium therebetween. The absorbent assembly also has generally opposite side edges and generally opposite end edges. A pair of stretchable side panels are joined to each one of the side edges to form with the absorbent assembly a waist opening and a pair of leg openings. A gathering means is joined along at least a portion of each leg opening for gathering that portion. The stretchable side panels provide generally inwardly directed force vectors against a wearer to maintain the garment snugly against the wearer's body and the absorbent assembly snugly in place against the crotch area both before and after a discharge.

51 Claims, 10 Drawing Sheets

4,940,464

DISPOSABLE INCONTINENCE GARMENT OR TRAINING PANT

This is a continuation application of application Ser. No. 133,674, filed on Dec. 16, 1987, now abandoned.

BACKGROUND OF THE INVENTION

This invention pertains to an absorbent garment, and more particularly to an absorbent garment for use as a child's training pant, adult incontinence garment, baby diaper and the like.

Currently, disposable absorbent garments find widespread use for infant care and adult incontinence care, and have generally replaced the use of reusable cloth absorbent garments, such as cloth diapers. The typical disposable absorbent garment is a three-layered composite structure comprising a liquid-permeable bodyside liner, a liquid-impermeable outer cover and an absorbent batt disposed between the bodyside liner and the outer cover. Materials now in general use for the three principal elements of a disposable absorbent garment include various types of nonwoven fabrics for the bodyside liner, a thin thermoplastic film for the outer cover and cellulosic fluff for the absorbent batt.

As one type of a disposable absorbent garment, diapers presently on the market are flat open-sided garments that are intended to be fit about an infant while lying down. A diaper is meant for use when the child is young and dependent upon a parent for fitting the diaper on the child.

The popularity of disposable diapers has led us to believe there is a demand for a disposable training pant that can be used when a child grows out of a diaper. Diapers are typically used with infants up to about 15 months old. When a child reaches an age in the range of about 15 to 30 months, a parent generally desires to start toilet training so the child can become independent of the parent. The training pant is intended for use when the child has reached an age at which he or she is ready to graduate to an underpant type of garment as a replacement for disposable diapers previously used. Thus, a suitable training pant must be a garment having closed sides so that a child can raise and lower the garment as necessary without requiring the aid of a parent. At the same time, a training pant must provide features of liquid and solid absorbency and prevent leakage of the waste fluids.

Cloth training pants, although widely used, have disadvantages. Current cloth training pants have very little absorbency and often must be used with exterior rubber or plastic pants. When a child wets a cloth training pant, most often all of the child's clothes must be changed. Further, if a child has a bowel movement, it is difficult to remove a cloth pant without making a mess, and the pant must be soaked and bleached. All of these factors can make the toilet training process frustrating for both child and parent.

Moreover, it is believed that the psychology of the toilet training stage is such that the child should perceive he or she is graduating to a garment that is different than a disposable diaper. It is evident that there is a need for a child's disposable training pant that meets the above requirements regarding fit, leakage, and psychology of toilet training.

As another type of disposable absorbent article, some of the currently-used incontinence products for adults and older children have been found unsatisfactory due to their bulkiness and ineffectiveness. Many of these garments are formed by folding flat sheets into a diaper-like structure that is bulky, particularly in the crotch portion. This type of garment further has a tendency to become dislodged during activity. Clearly, for the active person, these diaper-type garments are not desirable since they are bulky and interfere with the movements of the individual and the wearing of ordinary clothes. Furthermore, the large amounts of material utilized requires these adult diaper-type garments to be relatively expensive.

SUMMARY OF THE INVENTION

In one form of the invention, there is provided a disposable pant-like garment for absorbing human discharge, comprising an absorbent assembly including a liquid impervious outer cover, a liquid pervious bodyside liner and an absorbent medium. The absorbent assembly further includes generally opposite side edges and generally opposite end edges. A pair of stretchable side panels are joined to the side edges of the absorbent assembly forming waist and leg openings. A gathering means is joined at least along a portion of each leg opening for gathering that portion about the leg of a wearer.

BRIEF DESCRIPTION OF THE DRAWINGS

The above-mentioned and other features and objects of this invention and the manner of attaining them will become more apparent, and the invention itself will be better understood by reference to the following description of the invention taken in conjunction with the accompanying drawings, wherein.

DETAILED DESCRIPTION

Figure 1:
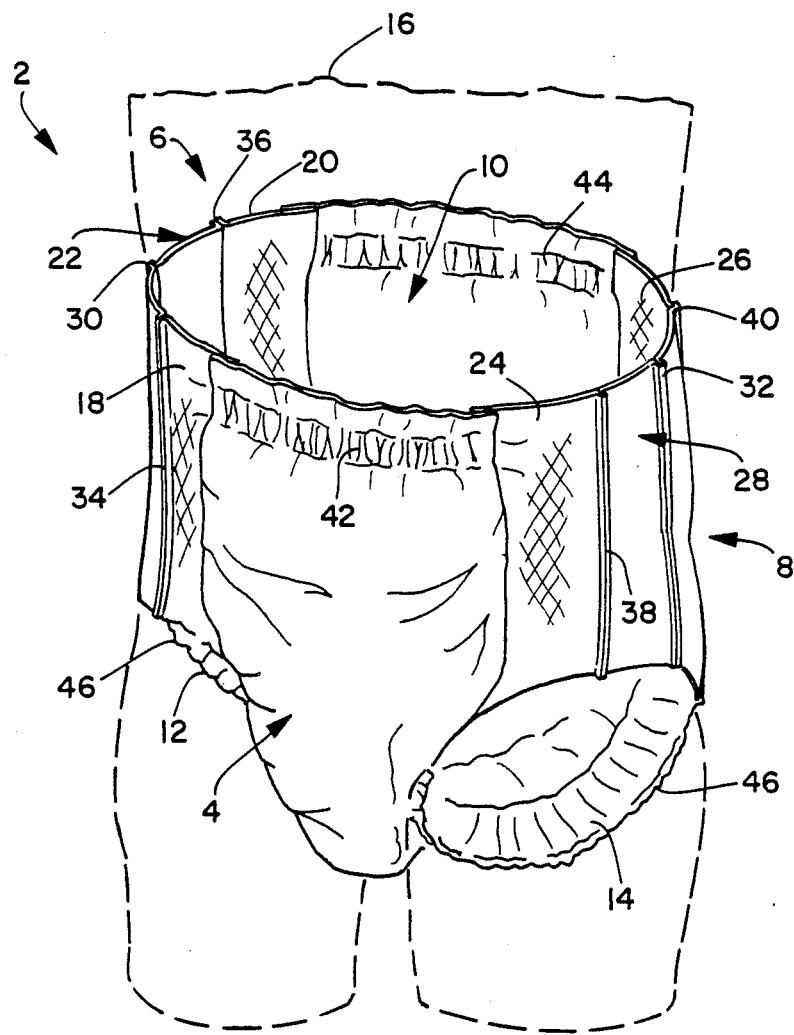
FIG. 1 is a perspective view of one embodiment of a garment or pant as it would appear on a wearer indicated in dashed lines.
Figure 3:
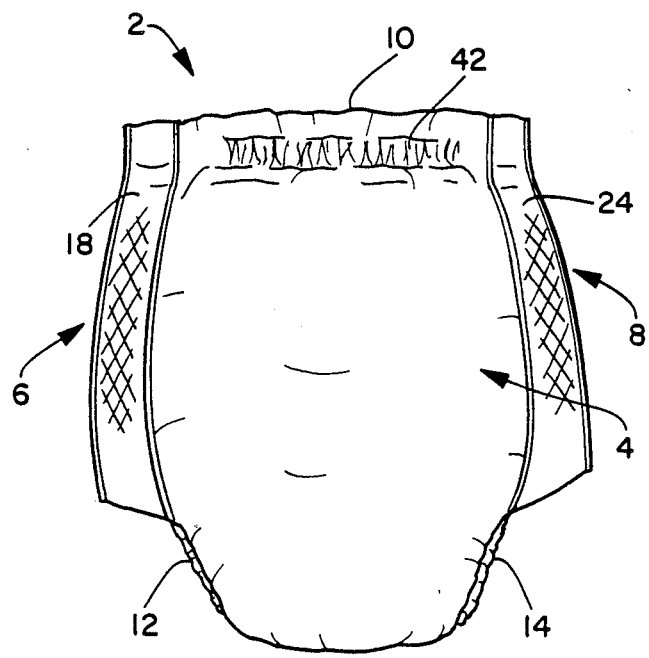
FIG. 3 is a front elevational view of the embodiment in FIG. 1.
Figure 4:
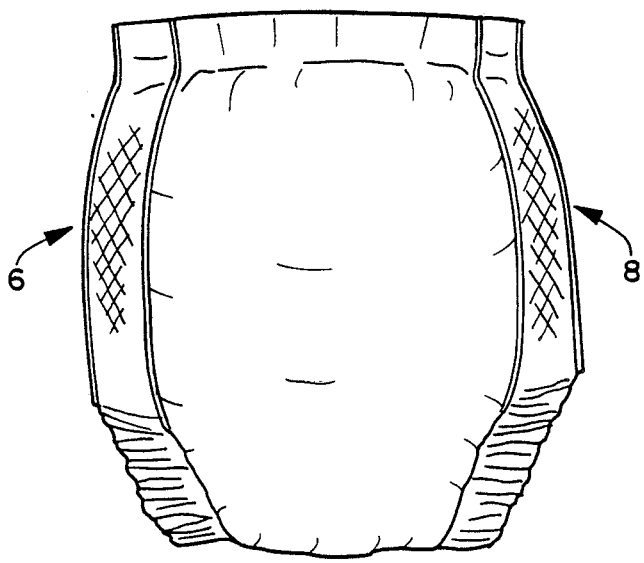
FIG. 4 is a front elevational view of the embodiment in FIG. 2.

Referring to FIGS. 1 and 3, there is illustrated one embodiment designated absorbent garment 2. Garment 2 generally comprises waste containment section 4 and two side panels 6, 8 defining a waist opening 10 and a pair of leg openings 12, 14. The total surface area of both side panels 6, 8 comprises about 20% to about 80% of the total surface area of garment 2, preferably about 25% to about 50%, and more preferably about 35% to about 45%. FIG. 1 illustrates absorbent garment 2 fitted on a wearer's torso portion 16 in dashed lines. Side panel 6 includes stretchable side member 18 and stretchable side member 20 connecting intermediate member 22 which is made of a nonstretchable material. Similarly, side panel 8 includes stretchable side member 24 and stretchable side member 26 connecting intermediate member 28 which is made of a nonstretchable material. As illustrated in FIG. 1, both intermediate members 22, 28 are made of two halves joined by respective seams 30, 32. Similarly, seam 34 joins stretchable side member 18 to intermediate member 22, seam 36 joins stretchable side member 20 to intermediate member 22, seam 38 joins stretchable side member 24 to intermediate member 28 and seam 40 joins stretchable side member 26 to intermediate member 28.

Hereafter, the terms "elasticity," "stretchability," and "elongation" will be interchangeably used to describe the properties of various materials. The meaning of these three words is intended to be the same, and that is that the material can be stretched and, upon relaxing, will tend to resume its original shape.

Garment 2 also includes front waist elastic member 42 and rear waist elastic member 44 for providing additional elasticity along waist opening 10. Leg elastics 46 are provided with waste containment section 4 between side panels 6, 8.

Figure 5:
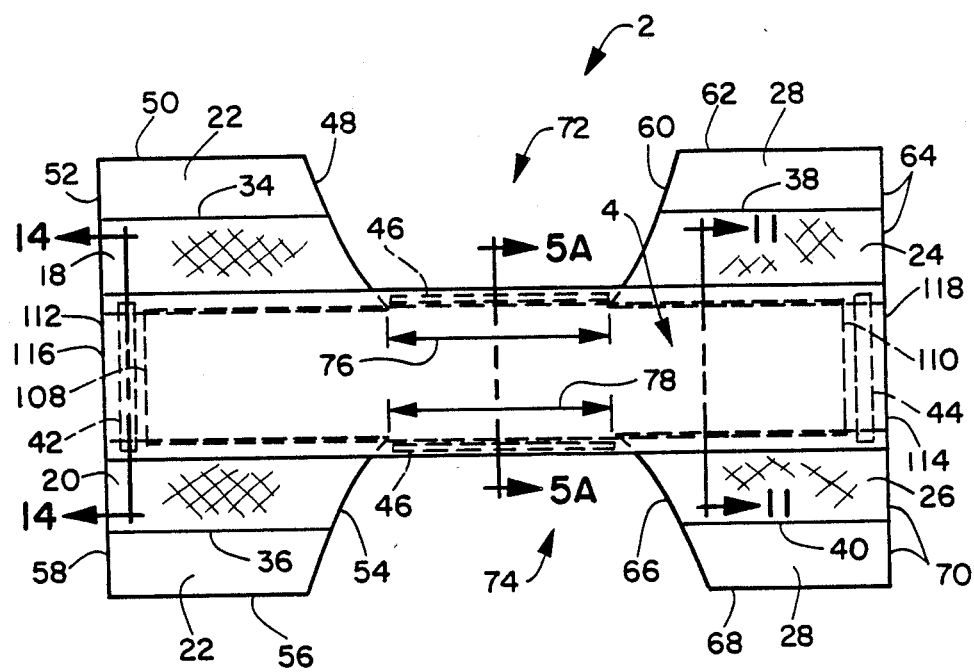
FIG. 5 is a top plan view of the embodiment of FIG. 1 in a flat condition with leg cut-outs before the seams are joined.

Referring now to FIG. 5, absorbent garment 2 is illustrated in a two-dimensional or planar configuration it assumes during the manufacturing process. Stretchable side member 18 is joined to waste containment section 4 and to a portion of intermediate member 22 at seam 34, and together form inner edge 48, side edge 50 and end edge 52. Similarly, stretchable side member 20 and its portion of intermediate member 22, which are joined at seam 36, form inner edge 54, side edge 56 and end edge 58. Although intermediate member 22 is illustrated in two halves in FIG. 5, it may be one integral member without a seam in the middle.

Stretchable side member 24 and its portion of intermediate member 28, which are joined at seam 38, form inner edge 60, side edge 62 and end edge 64. Stretchable side member 26 and its portion of intermediate member 28, which are joined at seam 40, form inner edge 66, side edge 68 and end edge 70. Again, intermediate member 28 can be of a form or geometry permitting it to be attached as one complete part to either stretchable side member 24 or 26, as opposed to being attached in two portions as illustrated in FIG. 5. Generally, the length of a side edge 50, 56, 62 or 68 is a function of the total garment length, e.g., a desired length of a side edge 50, 56, 62 or 68 is about 5% to about 50% of total garment length. A preferred length is about 15% to about 40% total garment length and a more preferred length is about 30% to about 40% total garment length. Total garment length is measured generally between end edge 52 and end edge 64, or between end edge 58 and end edge 70. Total garment length will generally be between about 12 inches to about 30 inches. Total garment width, as measured between edge 50 and edge 56 or between edge 62 and edge 68, is generally between about 6 inches to about 30 inches.

As described, leg cutout 72 is formed by inner edges 48, 60 and intermediate portion 76 of waste containment section 4 along leg elastic 46. Similarly, leg cutout 74 is formed by inner edges 54, 66 and intermediate portion 78 of waste containment section 4 along the other leg elastic 46. Although illustrated in FIG. 5 as being symmetrical about both its longitudinal and transverse axes, absorbent garment 2 may be varied in design or configuration by, for example, changing the dimension of intermediate portions 76, 78 or moving intermediate portions 76, 78 toward the front waist elastic member 42 or toward the waist elastic member 44. Any such redesign or reconfiguration will naturally be accompanied by a change in design or configuration of stretchable side members 18, 20, 24, 26 and intermediate members 22, 28. The design or configuration of absorbent garment 2 can also be varied by changing the curvatures of inner edges 48, 54, 60 and 66, such as by changing their radius of curvature.

Stretchable side members 18, 20, 24, 26 can be made of a single layer of a woven or nonwoven elastic or stretchable material, such as block copolymers of polystyrene, polyisoprene or polybutadiene, copolymers of ethylene, natural rubbers, urethanes, Kratons, and coextrusions/blends of the afore-mentioned. Other examples of suitable elastomeric materials include copolymers of ethylene, ethylene-vinyl acetate, ethylene-ethyl acetate, ethylene-acrylic acid, and ethylene-methyl acrylate and various percent blends of the copolymers of ethylene with polypropylene. Coextruded composites of ethylene-vinyl acetate, ethylene-ethyl acetate, ethylene-acrylic acid, ethylene-methyl acrylate, and polypropylene at various percents or mil thicknesses can also be used as the elastic material. Also, elastomeric staple integrated composites where staple fibers such as polypropylene, polyester, cotton or any other suitable staple fiber are integrated into an elastomeric meltblown web. Stretchable side members 18, 20, 24, 26 can also be a film of elastomeric material.

The above elastomeric materials may be formed by any suitable processes, such as film extrusion, spunbond process, meltblown process or the like.

Figure 9:
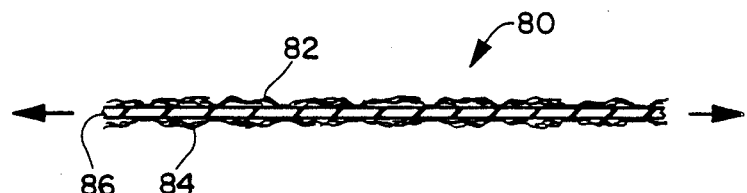
FIG. 9 is a fragmentary, side cross-sectional view of a stretch-bonded laminate in the stretched condition.
Figure 10:
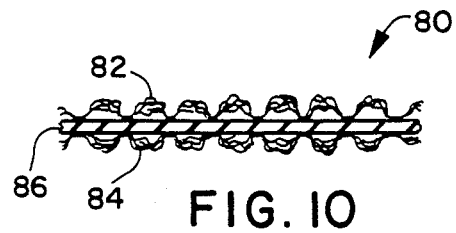
FIG. 10 is a fragmentary, side cross-sectional view of the stretch-bonded laminate of FIG. 9 in a relaxed condition.

Stretchable side members 18, 20, 24, 26 can also be a stretchbonded laminate that may have elasticity in all directions, and may be breathable, i.e., is pervious to vapors, but impervious to liquids. FIGS. 9 and 10 illustrate a stretch-bonded laminate 80 in the stretched and relaxed conditions, respectively. Stretchbonded laminate 80 generally comprises an outer layer 82, an inner bodyside layer 84 and an elastic layer 86 disposed between layers 82, 84. Although layers 82, 84 are described as outer and inner, respectively, they can be made of the same materials and thus be interchangeable.

Layers 82, 84 can be made of any woven or nonwoven material, and are preferably made of a nonwoven fibrous material. Examples of nonwoven fibrous material include variously bonded polyolefin fibers such as thermally-bonded polypropylene, polyethylene, polyester; spunbonded polypropylene, spunbonded polyethylene or blends thereof; meltblown polypropylene, meltblown polyethylene or blends thereof; bonded carded webs of synthetic or natural fibers or blends thereof; extruded films of thermoplastic materials; and the like. Naturally, copolymers of polyolefin or other material fibers may also be utilized.

Elastic or stretchable layer 86 is preferably a meltblown or film of block or graft copolymers such as butadiene, isoprene, styrene, ethylene-methyl acrylate, ethylene-vinyl acetate, ethylene-ethyl acrylite or blends thereof. One preferred elastomeric is a block copolymer of styrene-ethylbutadiene-styrene. Other types of materials of which elastic layer 86 can be made are a meltblown or film of block or graft copolymers such as butadiene, isoprene, styrene, ethylene-methyl acrylate, ethylene-vinyl acetate, ethylene-ethyl acrylite or blends thereof. One preferred elastomeric is a block copolymer of styrene-ethylbutadiene-styrene. Other types of materials of which elastic layer or stretchable layer 86 can be made are the Kraton G series from The Shell Chemical Company such as Kraton G-1650, Kraton G-1652, Kraton GX-1657 and preferably Kraton G-2740X. Also, the Kraton D series can be used, as well as polyester elastomeric materials, polyurethane elastomeric materials and polyamide elastomeric materials. It should be pointed out that the stretchable or elastomeric materials of which side panels 6, 8 are made can also be used for layer 86, and the just-described stretchable or elastomeric materials of which layer 86 can be made may also be used to make side panels 6, 8.

Typically, a stretch-bonded laminate is made by stretching the elastic or stretchable layer to a selected elongation; placing a non-stretched layer or layers on the stretched elastic layer; bonding the layers together and allowing the layers to relax so that the elastic layer gathers the other layer or layers.

Figure 11:
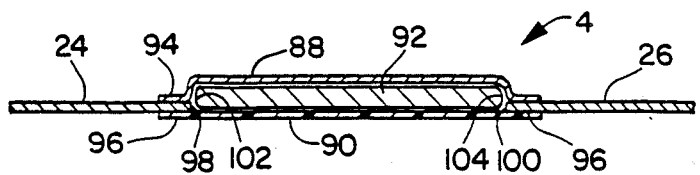
FIG. 11 is a sectional view of FIG. 5 taken along line 11—11 and viewed in the direction of the arrows.

Referring now to FIG. 11, which is a cross-section through FIG. 5, the attachment of waste containment section 4 with stretchable side members 18, 20, 24, 26 will be described. Waste containment section 4 generally comprises a liquid pervious bodyside liner 88, a liquid impervious outer cover 90 and an absorbent medium 92 between liner 88 and cover 90. Outer cover 90 can be a woven or nonwoven material, films, or a film-coated nonwoven material comprising cast or blown films of polyethylene, polypropylene, polyester or blends thereof. Outer cover 90 may also be a composite of a bonded carded or spunbonded or meltblown material, for example, a spunbonded-meltblown composite of thermoplastic material or a spunbonded-meltblown-spunbonded thermoplastic material, wherein the spunbonded layer can provide a cloth-like texture and the meltblown layer can provide liquid impermeability. Materials of which outer cover 90 can be made include nonwovens having a high basis weight, such as about 0.4 ounces per square yard, about 10 grams per square meter or basis weights greater than the aforementioned.

Outer cover 90 can also be extruded films of polyolefin polymers or copolymers, or other thermoplastic materials. Generally outer cover 90 will have a length from about 12 inches to about 30 inches, and a width from about 3 inches to about 20 inches.

Bodyside liner 88 can be a woven material, or a nonwoven material such as any flexible porous sheet of polyolefin fibers, such as polypropylene or polyethylene or polyester fibers; a web of spunbonded polypropylene or polyethylene or polyester fibers; a web of rayon fibers; a bonded carded web of synthetic or natural fibers or blends thereof. Liner 88 can also be an apertured plastic film. Liner 88 generally will have a length from about 12 inches to about 30 inches, and a width from about 3 inches to about 20 inches.

Absorbent medium 92 can be made of wood pulp fluff or a mixture of wood pulp fluff and a superabsorbent material, or a wood pulp fluff integrated with a thermoplastic absorbent material treated with a surfactant. Thermal binders, such a Pulpex ®can be used in blends or layering with the fluff and superabsorbent. Medium 92 can also be a batt of meltblown synthetic fibers, a bonded carded web of synthetic or natural fibers or blends thereof, a composite of meltblown fibers and the like. The synthetic fibers can be, but are not limited to, polypropylene, polyethylene, polyester and copolymers of these or other polyolefins. Medium 92 generally will have a length from about 3 inches to about 30 inches, and a width from about 3 inches to about 20".

As illustrated in FIG. 11, outer cover 90 and bodyside liner 88 sandwich absorbent medium 92, which is preferably adhered only to outer cover 90 by any suitable adhesive or other means. Alternatively, absorbent medium 92 could be joined to bodyside liner 88 or both bodyside liner 88 and outer cover 90. The longitudinal edge portions 94 of bodyside liner 88 and the longitudinal edge portions 96 of outer cover 90 also sandwich respective edge portions of stretchable side members 24, 26 to join them to waste containment section 4. Stretchable side members 24, 26 can be joined or adhered between respective edge portions 94, 96 by heat sealing, ultrasonic sealing, adhesive sealing or by other conventional means, such as stitching and the like.

As illustrated in FIG. 11, stretchable side members 24, 26 have respective inner sides 98, 100 that are illustrated as being just slightly spaced apart from respective absorbent sides 102, 104. One of the unique features of the present invention is the positional relationship between inner sides 98, 100 and absorbent sides 102, 104. Depending on the degree of elasticity and the amount of gathering desired, inner sides 98, 100 can be positioned at different distances from respective absorbent sides 102, 104. For example, inner sides 98, 100 can be in direct abutment against absorbent sides 102, 104 to provide maximum gathering, or inner sides 98, 100 can be spaced apart from respective absorbent sides 102, 104 as desired. A desired range of distances between inner sides 98, 100 and respective absorbent sides 102, 104 is about 0 inches to about 2 inches. A preferred range of distance between inner sides 98, 100 and absorbent sides 102, 104 is about 0 to about 1 inch, and a more preferred distance is about 0 to about ½ inch.

When inner sides 98, 100 are in abutment against absorbent sides 102, 104, the effect is to provide additional seal against leakage, and to allow for a more uniform transition from side panel to absorbent.

As inner sides 98, 100 are spaced an increasing distance from absorbent sides 102, 104, the resulting effect is to allow additional flexibility to the leg gasketing at each leg opening.

Figure 12:
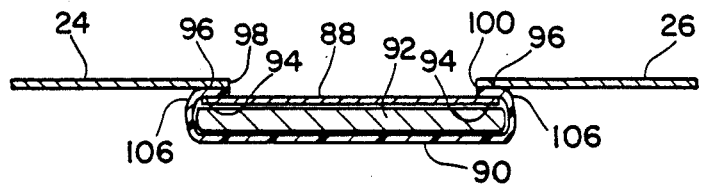
FIG. 12 illustrates a modification of the view of FIG. 11.

Referring to FIG. 12, there is illustrated a modification to the structure of FIG. 11. The longitudinal edge portions 94 of bodyside liner 88 terminate substantially at absorbent sides 102, 104. Longitudinal edge portions 96 of outer cover 90 overlap absorbent sides 102, 104 and edge portions 94 to form liquid-impervious baffles 106. Stretchable side members 24, 26 are then joined on top of edge portions 96, which form baffles 106, such that edge portions 96 of outer cover 90 are joined between respective stretchable side members 24, 26 and bodyside liner 88. As illustrated in FIG. 12, inner sides 98, 100 are substantially coincident with the remote ends of edge portions 94. If desired for better fluid control, baffles 106, which again are the overlapping edge portions 96 of outer cover 90, can extend further inwardly over bodyside liner 88 and beyond inner sides 98, 100, thereby creating larger baffles 106. By so extending baffles 106 toward the central portion of absorbent medium 92, there is a reduction in the amount of fluid flowback that may occur in both the longitudinal and transverse directions, thereby further reducing the chance of any fluid leakage about the leg openings 12, 14.

Figure 13:
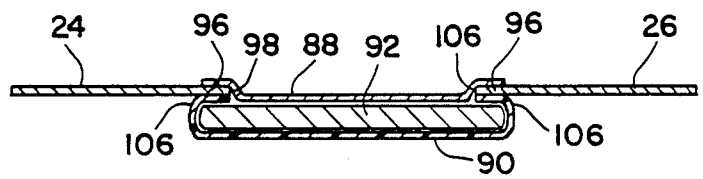
FIG. 13 illustrates a modification of the view of FIG. 11.

Referring to FIG. 13, another modification of FIG. 11 is illustrated. In this particular modification, edge portions 96 of outer cover 90 overlap only absorbent medium 92. Stretchable side members 24, 26 are then attached to the top of edge portions 96, again which form baffles 106, and bodyside liner 88 is then attached to stretchable side panels 24, 26. As illustrated in FIG. 13, inner sides 98, 100 are substantially coincident with the ends of edge portions 96. However, edge portions 96, forming baffles 106, can extend further inwardly toward the center of absorbent medium 92, thereby providing greater protection against fluid flowback in both the longitudinal and transverse directions.

The percentage of overlap or coverage of absorbent medium 92 with baffles 106 can be 0 to about 99%, preferably about 10% to about 50%, and more preferably about 10% to about 20%.

As baffles 106 are disposed further inwardly toward the center of absorbent medium 92, inner sides 98, 100 can likewise be extended further inwardly before being joined to edge portions 96. The percent overlap or coverage of panel inner sides 98, 100 with absorbent medium 92 can be 0 to about 50%, preferably about 3% to about 20%, and more preferably about 6% to about 12%.

With reference to FIGS. 12, 13, side panels 24, 26 alternatively can be attached to the bottom surface of outer cover 90.

As described above, waste containment section 4 of absorbent garment 2 is maintained in a snug-fitting, comfortable fashion against the wearer by elastic or stretchable side panels 6, 8. The effect of side panels 6, 8, and leg elastics 46 extending about the inner portion of the wearer's legs, is to provide not only vertical forces that maintain the waste containment section 4 against the wearer's crotch area, but also inwardly directed horizontal force vectors against the hips and mid-section that hold or hug waste containment section 4 against the sides of the wearer, both before and after a void.

Referring to FIG. 5, waist elastics 42, 44 are illustrated with absorbent garment 2 in a two-dimensional or planar form before the construction of seams 30, 32. Ends 108, 110 of absorbent medium 92 terminate short of outer cover ends 112, 114 and bodyside liner ends 116, 118. Absorbent ends 108, 110 are spaced a distance from outer cover ends 112, 114 in the range of about ⅛ inch to about 2 inches. Generally, bodyside liner ends 116, 118 are substantially coincident with outer cover ends 112, 114, and the total garment length is measured between these ends. It may be that bodyside liner ends 116, 118 extend beyond outer cover ends 112, 114 and are folded over ends 112, 114 to form a skirt or fringe about waist opening 10. In this case, the total garment length is measured between ends 112, 114. Similarly, outer cover ends 112, 114 could extend beyond bodyside liner ends 116, 118 and be folded thereover, and the total garment length is measured between ends 116, 118.

Preferably, waist elastics 42, 44 are made of an activatable elastic material applied in an unstretched condition. Thereafter, waist elastics 42, 44 are activated, such as by heat, light, moisture or the like, so as to retract and become elastic. Types of these activatable elastic materials can be purchased from the Minnesota Mining and Manufacturing Company.

Each waist elastic 42, 44 can be a single ribbon of elastic material that is suitably adhered solely to bodyside liner 88, or to outer cover 90, or to both liner 88 and cover 90. A single ribbon of waist elastic 42 or 44 in the relaxed, attached condition has a length of about 2 inches to about 12 inches and a relaxed, attached width of about ⅛ inch to about 2 inches. Generally, waist elastic 42, 44 will be adhered in a stretched condition, and in the stretched condition, each waist elastic 42, 44 will have a stretched length of about 2¼ inches to about 15 inches and a stretched width of about ⅛ inch to about 1⅝ inches. These parameters should provide a relaxed, attached length of about 50% to about 100% of the width of waste containment section 4.

Instead of each waist elastic 42, 44 being a single ribbon of elastic material, each may be comprised of a multiple strand of ribbons having a generally rectangular cross-section or ropes having a generally circular cross-section. For example, if each waist elastic 42, 44 comprises multiple strands of ribbons, each of the ribbons in the strand will have a length similar to that for a single ribbon and a width from about ⅛ inch to about ¾ inch. If each waist elastic 42, 44 comprises multiple strands of rope elastics, each rope preferably has a length similar as above and a width or diameter from about 0.04 inch to about 0.25 inch.

Waist elastics 42, 44 may be made of any suitable elastic material, such as those of which side panels 6, 8 or stretchable layer 86 can be made. Suitable adhesives for adhering waist elastics 42, 44 to absorbent garment 2 include hot melt adhesives, spray adhesives, self-adhering elastomeric materials and the like.

Figure 14:
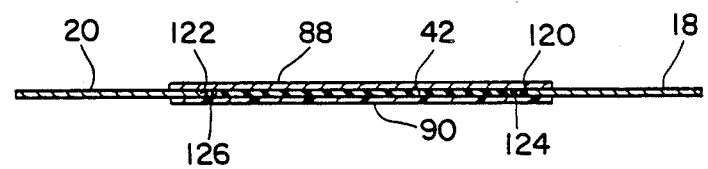
FIG. 14 is a sectional view of FIG. 5 taken along line 14—14 and viewed in the direction of the arrows.
Figure 15:
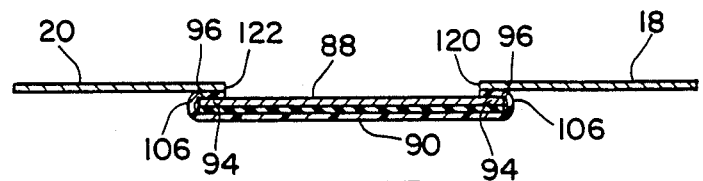
FIG. 15 illustrates a modification of the view of FIG. 14.
Figure 16:
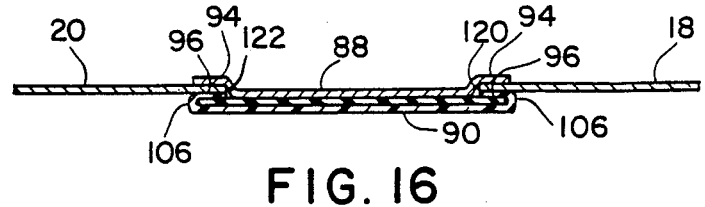
FIG. 16 illustrates a modification of the view of FIG. 14.

Referring now to FIGS. 14–16, the various seam configurations for waist elastics 42, 44 will be described. Since both waist elastics 42, 44 can be attached in a similar manner, only a description with reference to waist elastic 42 will be made with the understanding that it also applies to waist elastic 44. In FIG. 14, waist elastic 42 is sandwiched between bodyside liner 88 and outer cover 90. Similarly, stretchable side members 18, 20 are sandwiched between bodyside liner 88 and outer cover 90, with inner sides 120, 122 abutting against respective waist elastic sides 124, 126. The attachment of waist elastic 42 and stretchable side members 18, 20 to bodyside liner 88 and outer cover 90 can be made by heat sealing, ultrasonic sealing, adhesive sealing or any other suitable means. In FIG. 14, inner sides 120, 122 abut against respective waist elastic sides 124, 126 in order to provide a continuous stretchable or elastic effect about the periphery of waist opening 10. However, inner sides 120, 122 can be spaced from respective waist elastic sides 124, 126 in the range of about 0 inches to about 2 inches. A preferred range is from about 0 inches to about 1 inch, and a more preferred range is from about 0 to about ½ inch. Also, side panel inner sides 120, 122 could overlap partially or completely waist elastics 42, 44 in that area between ends 116, 108 and ends 118, 110.

Referring now to FIG. 15, the sides of waist elastic 42 and bodyside liner 88 are substantially coincident, and the longitudinal edge portions 96 of outer cover 90 are folded to overlap longitudinal edge portions 94 of bodyside liner 88, thereby forming baffles 106. Stretchable side members 18, 20 are then adhered to the exposed tops of baffles 106, such that inner sides 120, 122 are substantially coincident with the ends of baffles 106. Baffles 106 can be extended further inwardly toward the center portion of bodyside liner 88 and absorbent medium 92. The percent of overlap or coverage of baffles 106 with absorbent medium 92 can be in the range of about 0% to about 90%. Preferably, the coverage is about 5% to about 50% and more preferably from about 8% to about 13%.

Referring now to FIG. 16, longitudinal edge portions 96 of outer cover 90 overlap waist elastic 42 to form baffles 106, and stretchable side members 18, 20 are then adhered to baffles 106. Bodyside liner 88 is disposed over waist elastic 42 and inner sides 120, 122 of stretchable side members 18, 20. Baffles 106 can extend over elastic 42 as described above with reference to FIG. 15.

Referring now to FIG. 5, leg elastics 46 may be made of the same or other described materials of which waist elastics 42, 44 can be made. Leg elastics 46 may be similarly adhered by one of those methods described for adhering waist elastics 42, 44. Each leg elastic 46 is preferably a single ribbon of elastic material having a relaxed, attached length of about 1 inch to about 18 inches and a relaxed, attached width of about ⅛ inch to about 3 inches, and an elongation of about 25% to about 350%. A preferred length is about 2 inches to about 9 inches and an elongation of about 30% to about 260%. A more preferred length is about 3 inches to about 4 inches and an elongation of about 125% to about 200%. A preferred relaxed width is about ¼ inch to about 1½ inches, and a more preferred width is about ½ inch to about 1 inch.

As a percentage of total garment length, the relaxed, attached elastic 46 has a length of about 10% to about 100% of total garment length. A preferred length is about 10% to about 50%, and a more preferred length is about 15% to about 25%.

As with waist elastics 42, 44, leg elastics 46 do not necessarily need to be a single ribbon of elastic material, but can be multiple strands of ropes or ribbons of elastic material. If elastics 46 are rope-like, preferred diameters are between about 0.04 inches to about 0.25 inches.

Figure 5A:
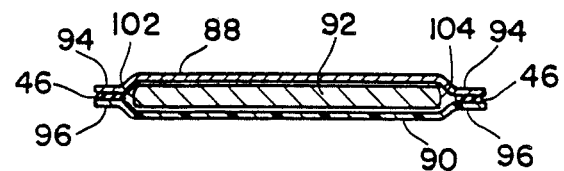
FIG. 5A is a sectional view of FIG. 5 taken along line 5A—5A.

Referring to FIG. 5A, leg elastics 46 are positioned between longitudinal edge portions 94 of bodyside liner 88 and longitudinal edge portions 96 of outer cover 90. Leg elastics 46 can abut against or be spaced apart from respective absorbent sides 102, 104. Leg elastics 46 can be spaced from absorbent sides 102, 104 from about 0 to about 2 inches. A preferred range is from about 0 to about 1 inch, and a more preferred range is from about 0 to about ½ inch.

Figure 5B:
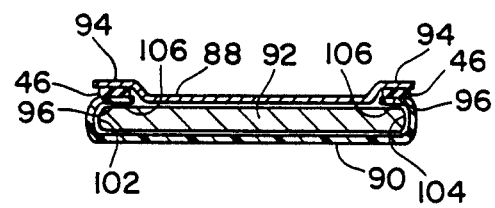
FIG. 5B is a modification of the view in FIG. 5A.

FIG. 5B illustrates a modification of the placement of leg elastics 46. In this modification, outer cover 90 is wrapped around absorbent edges 102, 104 so as to overlap and form baffles 106. Leg elastics 46 are then positioned on top of baffles 106, which are also longitudinal edge portions 96, and bodyside liner 88 is then disposed over leg elastics 46.

Figure 5C:
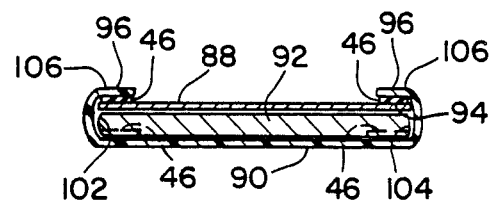
FIG. 5C is a modification of the view in FIG. 5B.

Similarly, FIG. 5C illustrates leg elastics 46 being positioned on top of longitudinal edge portions 94 of bodyside liner 88, and with outer cover 90 then overlapping leg elastics 46 to form baffles 106.

Leg elastics 46 can extend inwardly of or overlap absorbent sides 102, 104 a distance that is from about 0% to about 50% of the maximum width of absorbent medium 92; a preferred distance is from about 3% to about 20%, and a more preferred distance is from about 6% to about 12% of the maximum width of absorbent medium 92.

Also, in both modifications illustrated in FIGS. 5B and 5C, leg elastics 46 may be positioned below absorbent medium 92, as illustrated in dashed lines in FIG. 5C. In this case, leg elastics 46 would be positioned between outer cover 90 and absorbent medium 92. In FIG. 5A, leg elastics 46 can also be positioned either above or below absorbent medium 92.

Figure 6:
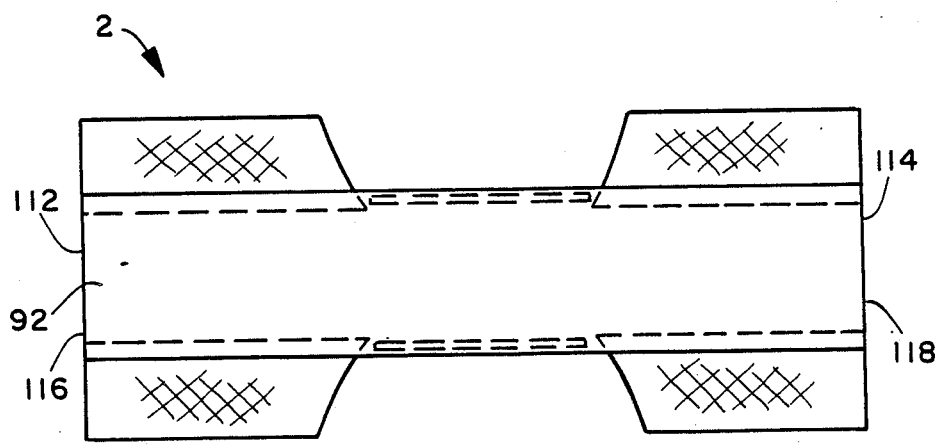
FIG. 6 is similar to FIG. 5 and has the nonelastic intermediate panel and waist elastics removed.

Referring now to FIG. 6, there is illustrated a modification of the embodiment in FIG. 1 wherein waist elastics 42, 44 and nonstretchable intermediate members 22, 28 are absent. Also, absorbent medium 92 extends to and is substantially coincident with outer cover ends 112, 114 and bodyside liner ends 116, 118. In all other respects, the modification in FIG. 6 is identical to FIG. 5. The absorbent garment 2 formed from the modification in FIG. 6 would be the same as that illustrated in FIG. 1, but without the waist elastics 42, 44 and the intermediate members 22, 28. This modification can be used for smaller torsos because of the removal of intermediate members 22, 28 or, if additional elasticity is desired, then intermediate members 22, 28 are replaced by extending stretchable side members 18, 20, 24, 26.

Figure 7:
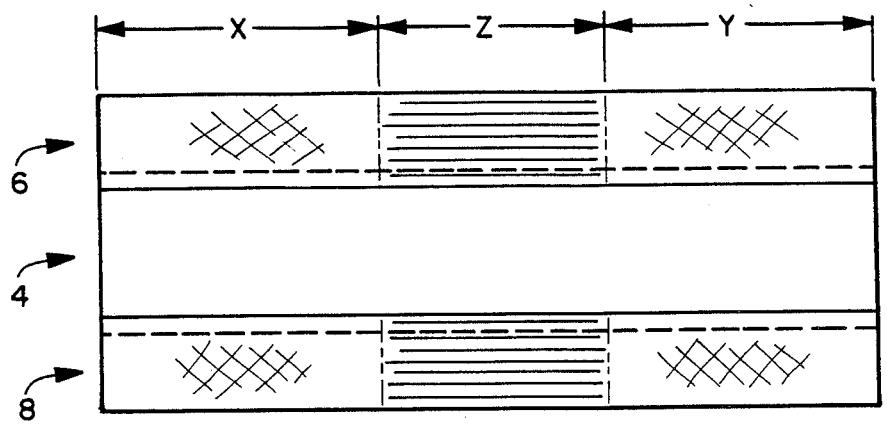
FIG. 7 is a top plan view of the embodiment of FIG. 2 in a flat condition before the seams are joined.
Figure 8:
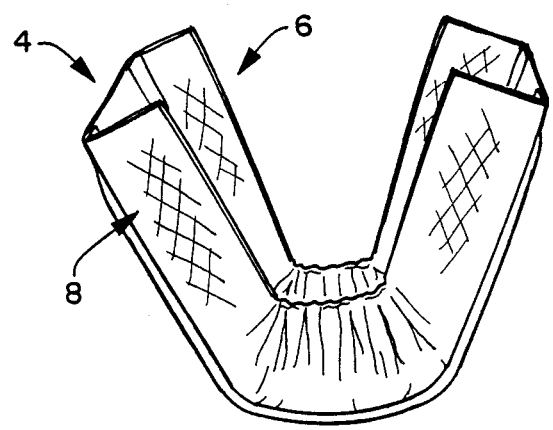
FIG. 8 is a side plan view of the embodiment of FIG. 7 in a partially folded form.

Another embodiment is illustrated in FIGS. 2, 4, 7 and 8 wherein leg elastics 46 have been replaced by side panels 6, 8, and intermediate members 22, 28 and waist elastics 42, 44 are absent. Each side panel 6, 8 is illustrated in FIG. 7 as comprising three areas indicated as X, Y, and Z. Those areas X, Y of side panels 6, 8 are attached to waste containment section 4 in a relaxed condition, while area Z of side panels 6, 8 are prestretched before being joined to waste containment section 4. The area Z is disposed intermediate the longitudinal ends of waste containment section 4, and upon being relaxed, the garment tends to assume the body-conforming shape illustrated in FIG. 8.

The present invention also contemplates use of leg elastics 46 in conjunction with side panels 6, 8 in the embodiment of FIGS. 2, 4, 7, and 8. Leg elastics 46 can abut, overlap, or be spaced apart from respective panels 6, 8.

As explained above, the garment of the present invention is designed to fit a large range of sizes merely by changing the dimensions of elastic side panels 6, 8, or by changing the type of elastic material of which side panels 6, 8 are made. Generally, the ranges of sizes can be varied by (1) selecting a material of elasticity and/or (2) by increasing the length and width dimensions of a given elastic material of which side panels 6, 8 are made. Side panels 6, 8 will generally have a width of about ½ inch to about 5 inches, and will be made of a material having an elongation or elasticity from about 10% to about 500%. Preferably, side panels 6, 8 will have a width from about 2 inches to about 3½ inches, and the material of which they are made will have an elasticity between about 50% to about 300%. In a more preferred embodiment, side panels 6, 8 will have a width of about 1¼ inches to about 2 inches and an elasticity from about 75% to about 200%.

Figure 17:
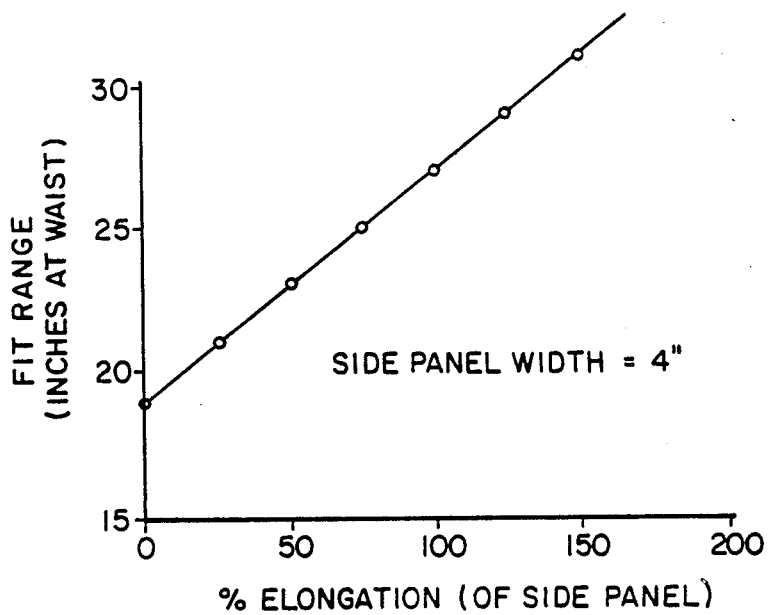
FIG. 17 is a graph of percent elongation of a side panel versus fit range of the waist in inches.
Figure 18:
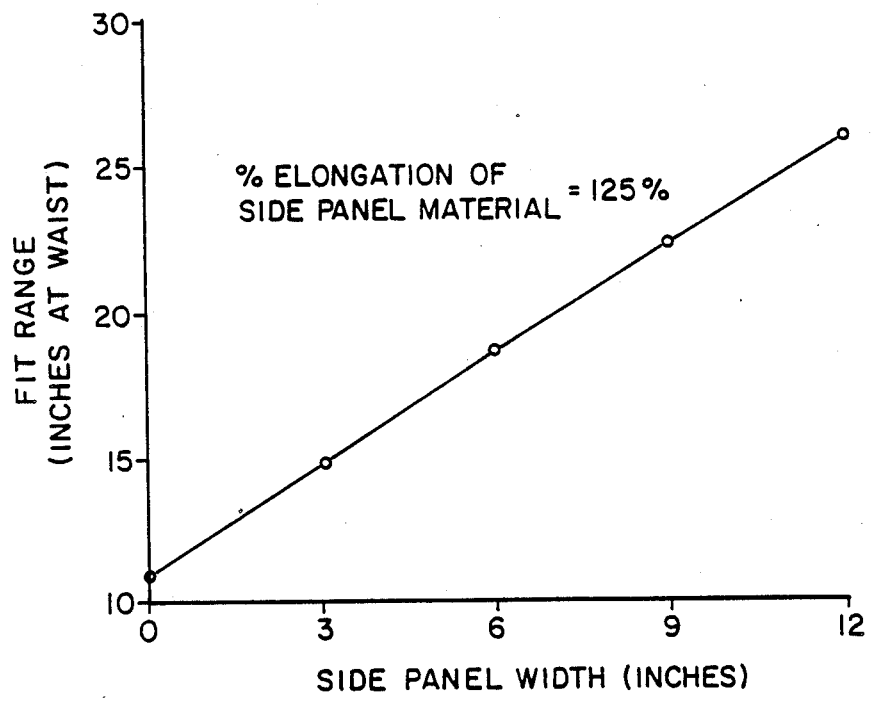
FIG. 18 is a graph of the side panel width in inches versus the fit range of the waist in inches.
Figure 19:
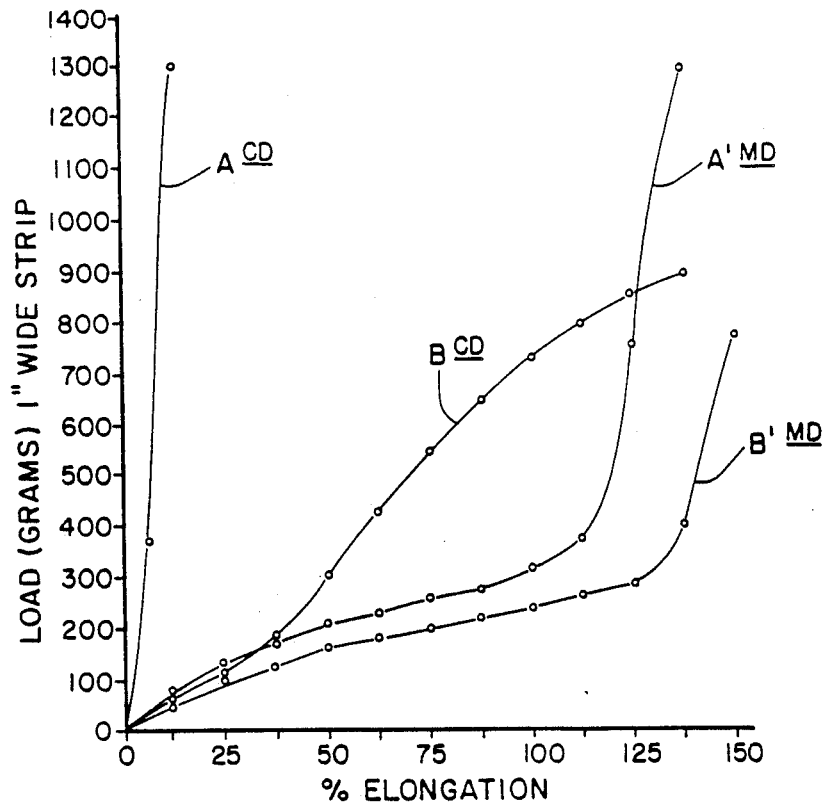
FIG. 19 is a graph of percent elongation versus the load in grams for a one inch wide strip of side elastic.

Referring to FIGS. 17–19, the relationships between side panels 6, 8 and the range of sizes of absorbent garment 2 are graphically illustrated. In FIG. 17, each side panel 6, 8 has a width of about 4 inches, and the percent elongation of the side panels is plotted against the fit range in inches at the waist. As illustrated, there is a generally linear relationship between the percent elongation of the elastic material of which side panels 6, 8 are made and the size range of the waist measured in inches.

FIG. 18 illustrates the relationship between side panel width and a fit range in inches at the waist for an elastic material having a percent elongation of 125%. As illustrated, there is a generally linear relationship between an increase in the side panel width in inches versus the fit range in inches at the waist.

FIG. 19 is a graph plotting percent elongation versus the load in grams on a 1-inch wide strip of elastic material. The load in grams measures the tension at elongation of the particular material, and this feature is maximized by theoretically have a slope of 0 for each plot. In FIG. 19, the plotted curves represent two elastic materials, wherein curve A represents the cross-direction stretch and curve A' represents the machine-direction stretch of one material; and curve B represents the cross-direction stretch and curve B' represents the machine-direction stretch of the other material. The machine-direction stretch, preferably in the stretch-bonded laminate embodiment, is the force vector applied horizontally inwardly or toward the hips and mid-section when worn. This stretch-strain relationship is important to the use and performance of the garment of the present invention. The side panel material must stretch to adjust to various sizes. The tension cannot be so high that the garment is difficult to use or be too tight during use. Nor, can it be so low in tension as not to maintain the product in position during use. Preferably, the materials of which side panels 6, 8 are made will have a tension range, i.e., load (grams) per 1 inch wide strips, from about 50 grams to about 1,000 grams. In a more preferred embodiment, the side panel materials would have a tension range of about 200 to about 500 grams per 1 inch wide strip. Secondly, curves A' and B' both illustrate relatively very gradual slopes between 0 and about 125% elongation or elasticity. The slope is important to maintain a constant fit tension at the various sizes. With a theoretical slope of 0, the tension of the product would be the same at the relaxed size as it would be at the fully-stretched size.

Figure 21:
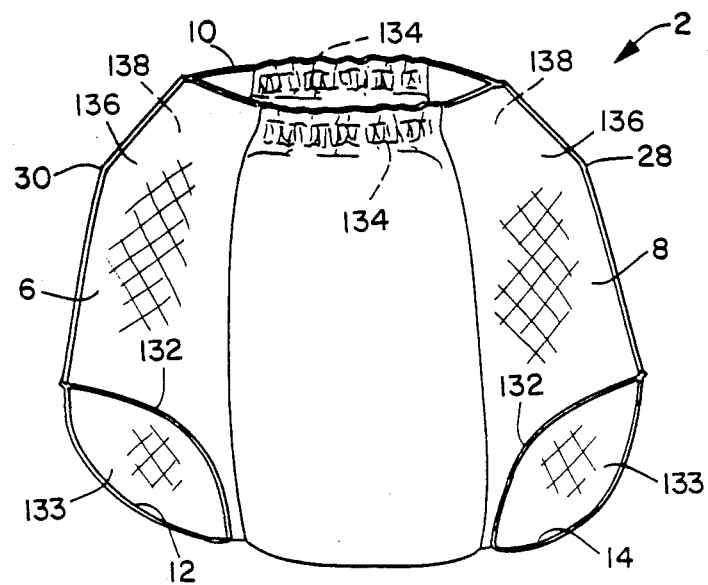
FIG. 21 illustrates yet another embodiment of a garment or pant.

Referring now to FIG. 21, there is yet another modification of absorbent garment 2 that includes waist elastics 134. A unique feature of this modification of absorbent garment 2 is the geometry of elastic side panels 6, 8. Specifically, it can be seen that the front portions 132 of leg openings 12, 14 are cut higher than the back portions 133 of leg openings 12, 14. The purpose for this particular geometry of leg openings 12, 14 is to improve further the fit of the garment. The added material in the back provides coverage of the buttocks, while in the front the cut is higher in following the curvature of the leg, thereby permitting freer leg movement.

The upper portions of elastic side panels 6, 8 are identified as remote end segments 136, 138, and they are cut so that they slope inwardly and upwardly from the intermediate portions of side panels 6, 8 toward waist opening 10. The purpose for this is to improve further the fit of the garment, especially when the user is disproportionate at the hips and waist. The design or configuration also assists in pulling the garment up in place. The length of each sloping end segment 136, 138 is from about 3% to about 40% of total garment length, preferably about 5% to about 25% of total garment length, and more preferably about 10% to about 15% of total garment length.

The angular slope, as measured with the vertical in FIG. 21, of end segments 136, 138 is from about 5° to about 55°, preferably from about 10° to about 40°, and more preferably from about 15° to about 30°.

Figure 20:
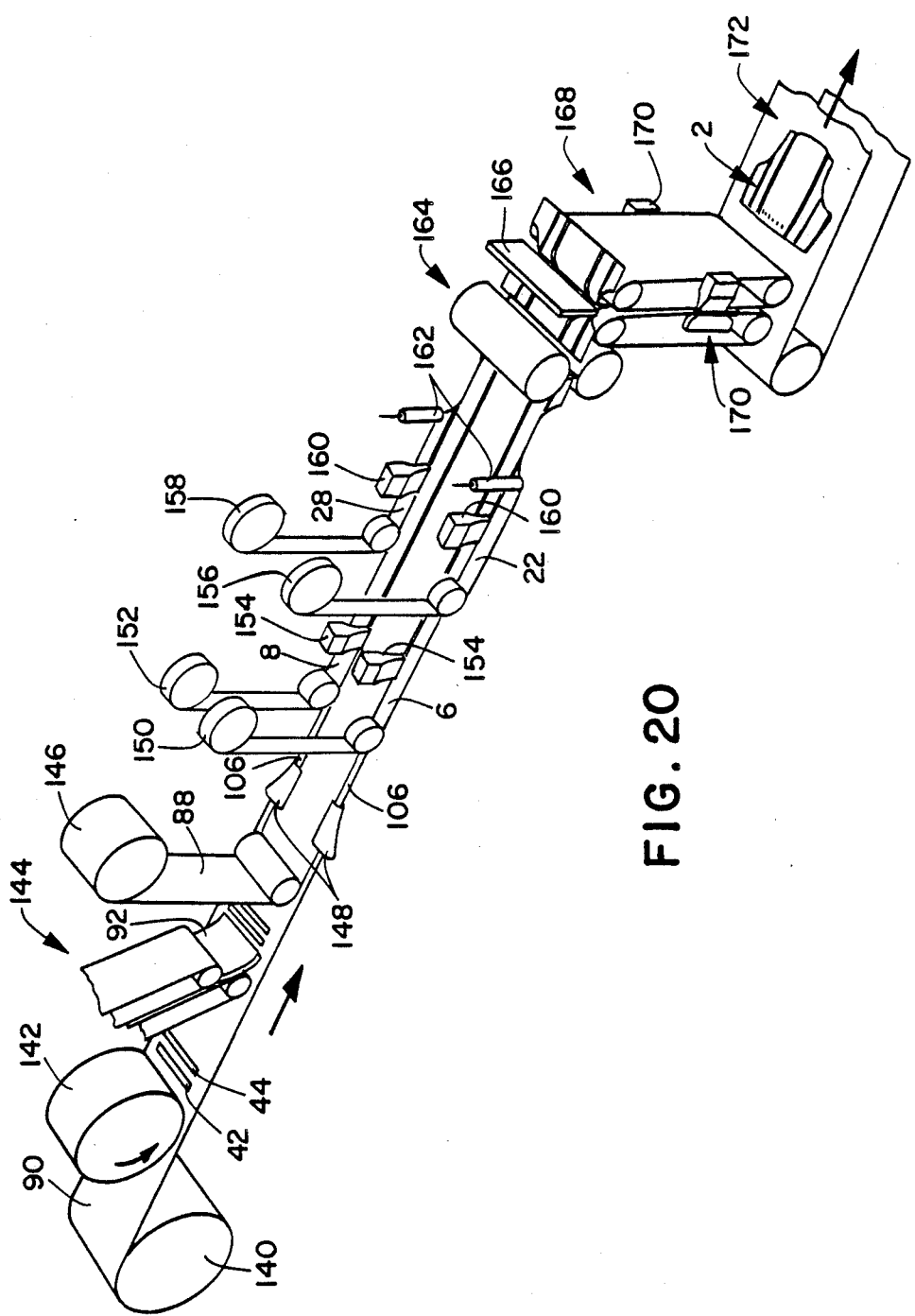
FIG. 20 is a schematic of one apparatus for producing one embodiment of a garment or pant.

Referring now to FIG. 20, a description will be made of one process for making one embodiment of garment 2. Supply roll 140 provides a continuous supply of outer cover 90 to supply drum 142, which attaches, if desired, waist elastics 42, 40 thereon. After application of waist elastics 42, 44, outer cover 90 continues to conveyor assembly 144 which positions absorbent medium 92 between waist elastics 42, 44. Thereafter, supply roll 146 delivers a continuous supply of bodyside liner 88 on top of waist elastics 42, 44, absorbent medium 92 and the continuous supply of outer cover 90. Folding bars 148 then fold outer cover 90, which has a width greater than the width of absorbent medium 92 and bodyside liner 88 to form baffles 106. After baffles 106 have been formed, supply rolls 150, 152 provide a continuous supply of elastic side panels 6, 8, and bonding station 154 then bonds, such as by ultrasonic, thermal, or adhesive bonding, elastic side panels 6, 8, bodyside liner 88 and outer cover 90. Similarly, supply rolls 156, 158 provide a continuous supply of intermediate members 22, 28, and bonding station 160 then bonds, such as by ultrasonic, thermal, or adhesive bonding, elastic side panels 6, 8 and intermediate members 22, 28. Leg cutout station 162, which can be pressurized fluid-jets or a rotary die cutter, then cuts side panels 6, 8 to form leg openings 12, 14. As the composite continues through the process, cutting station 164 severs the composite, which is then tucked or folded in half by tucker bar 166, which contacts an intermediate portion of a severed composite and moves it between the individual conveyors of conveyor assembly 168. Located in conjunction with conveyor assembly 168 is seam bonding station 170 which bonds, such as by ultrasonic, thermal, or adhesive bonding, elastic side panels 6, 8 to form seams 30, 32 of absorbent garment 2. Conveyor assembly 168 then delivers absorbent garment 2 to transfer conveyor assembly 172, which delivers absorbent garments 2 to the next handling station.

Figure 2:
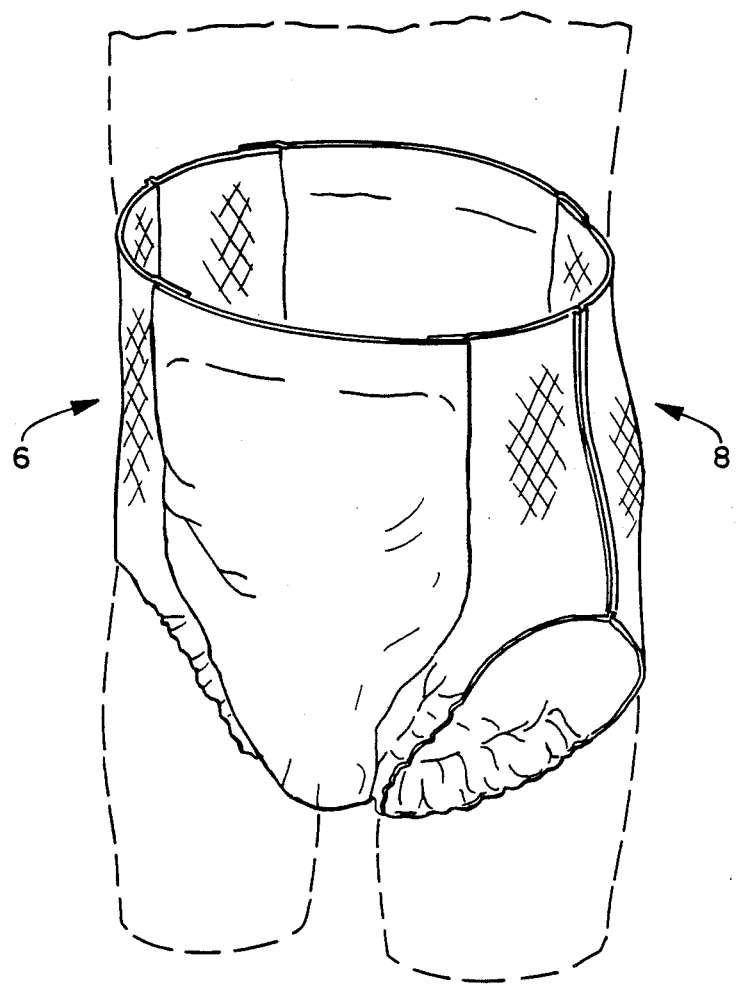
FIG. 2 is a perspective view of another embodiment on a wearer indicated in dashed lines.

The process illustrated in FIG. 20 can be easily adapted to make other embodiments of the present invention such as that illustrated in FIG. 2, and other constructions such as those illustrated in FIGS. 11–13.

While this invention has been described as having preferred embodiments, it will be understood that it is capable of further modifications. This application is therefore intended to cover any variations, uses or adaptations of the invention following the general principles thereof, and including such departures from the present disclosure as come within known or customary practice in the art to which this invention pertains and fall within the limits of the appended claims.

What is claimed is:

1. A disposable pant-like garment for absorbing human discharge comprising:
   an absorbent assembly comprising a liquid-impervious outer cover, a liquid-pervious liner, and an absorbent medium therebetween; said absorbent assembly further comprising generally opposite side edges and generally opposite end edges, stretchable side panels and said absorbent assembly being joined together to form a waist opening and a pair of leg openings, portions of said absorbent assembly side edges being generally adjacent respective said leg openings, said absorbent assembly end edges being generally adjacent said waist opening, and a gathering means being joined along a crotch portion of each said leg opening adjacent said absorbent assembly for gathering said crotch portion, a remaining portion of each said leg opening being relatively non-gathered, whereby said stretchable side panels provide generally inwardly directed force vectors against a wearer to maintain said garment snugly against the wearer's body and said absorbent assembly snugly in place against the crotch area both before and after a discharge, and said gathering means and said side panels provide elasticity about said leg openings to prevent leakage thereat.

2. The garment of claim 1 wherein said gathering means has a relaxed, attached length of about 10% to about 100% of the total length of said garment.

3. The garment of claim 2 wherein said gathering means has a relaxed, attached length of about 10% to about 50% of the total length of said garment.

4. The garment of claim 3 wherein said gathering means has a relaxed, attached length of about 15% to about 25% of the total length of said garment.

5. The garment of claim 1, wherein said gathering means has an elasticity of about 25% to about 350%.

6. The garment of claim 5 wherein said gathering means has an elasticity of about 30% to about 260%.

7. The garment of claim 6 wherein said gathering means has an elasticity of about 125% to about 200%.

8. The garment of claim 1, wherein each said gathering means is a plurality of elongate elastic members.

9. The garment of claim 1, wherein each said gathering means is pre-stretched when joined to its respective said leg opening.

10. The garment of claim 1, wherein each said gathering means is an integral extension of at least one of said stretchable side panels.

11. The garment of claim 10 wherein each said integral extension is pre-stretched when joined to said absorbent assembly.

12. The garment of claim 1, further comprising a pair of substantially non-stretchable side sections, each said side section being joined intermediate of a respective said stretchable side panel.

13. The garment of claim 1, wherein at least one of said stretchable side panels is manually tearable from said absorbent assembly.

14. The garment of claim 1, wherein each said stretchable side panel is a stretch-bonded laminate comprising a stretchable layer stretch-bonded to a gatherable layer, whereby upon relaxing said stretch-bonded layers, sad gatherable layer is gathered.

15. The garment of claim 14 wherein said stretch-bonded laminate comprises a second gatherable layer, said stretchable layer being stretch-bonded to said second gatherable layer, whereby upon relaxing said stretch-bonded layers, said second gatherable layer is gathered.

16. The garment of claim 1, or wherein at least an edge portion of each said gathering means is joined between said outer cover and said liner.

17. The garment of claim 1, or wherein edge portions of said gathering means directly abut against respective sides of said absorbent medium.

18. The garment of claim 16 wherein said gathering means edge portions are spaced apart from respective sides of said absorbent medium about 0 inches to about 2 inches.

19. The garment of claim 18 wherein said gathering means edge portions are spaced apart from said sides from about 0 inches to about 1 inch.

20. The garment of claim 19 wherein sad gathering means edge portions are spaced from said sides from about 0 inches to about ½ inch.

21. The garment of claim 16 wherein each said gathering means edge portion extends over a respective side of said absorbent medium a distance of about 0% to about 50% of the maximum width of said absorbent medium.

22. The garment of claim 21 wherein each said gathering means edge portion extends over a respective said side of said absorbent medium a distance of about 3% to about 20% of the maximum width of said absorbent medium.

23. The garment of claim 22 wherein each said gathering means edge portion extends over a respective said side of said absorbent medium a distance of about 6% to about 12% of the maximum width of said absorbent medium.

24. The garment of claim 1, wherein each said side panel has a tension range per inch of about 50 grams to about 1,000 grams.

25. The garment of claim 24 wherein each said side panel has a tension range per inch of about 200 grams to about 500 grams.

26. The garment of claim 1 wherein each said side panel has an elasticity of about 10% to about 500%.

27. The garment of claim 26 wherein each said side panel has an elasticity of about 50% to about 500%.

28. The garment of claim 27 wherein each said side panel has an elasticity of about 75% to about 200%.

29. The garment of claim 1, wherein said side panels comprise between about 20% to about 80% of the total surface area of said garment.

30. The garment of claim 29 wherein said side panels comprise between about 25% to about 50% of the total surface area of said garment.

31. The garment of claim 30 wherein said side panels comprise between about 35% to about 45% of the total surface area of said garment.

32. The garment of claim 1, wherein a relaxed, attached width of each said gathering means is between about ⅛ inch to about 3 inches.

33. The garment of claim 32 wherein the width of each said gathering means is between about ¼ inch to about 1½ inches.

34. The garment of claim 33 wherein the width of each said gathering means is between about ½ inch to about 1 inch.

35. The garment of claim 1, wherein said outer cover comprises at least two layers, the outermost one of said layers being made of a cloth-like material and the innermost one of said layers being made of a liquid-impervious material.

36. The garment of claim 1, further comprising a waist elastic at least at one end portion of said absorbent assembly.

37. The garment of claim 36 wherein said waist elastic comprises a plurality of elastic member.

38. A disposable pant-like garment for absorbing human discharge, comprising:
an absorbent assembly comprising a liquid-impervious outer cover, a liquid-pervious liner and an absorbent medium therebetween; said absorbent assembly further comprising generally opposite side edges and generally opposite end edges,
stretchable side panels and said absorbent assembly being joined together to form a waist opening and a pair of leg openings, portions of said absorbent assembly side edges being generally adjacent respective said leg openings, said absorbent assembly end edges being generally adjacent said waist opening,
respective portions of said stretchable side panels being generally peripherally disposed along respective portions of said leg openings, and
a gathering means being joined generally along the remaining crotch portion of each said leg opening for gathering sad crotch portion, whereby said stretchable side panels and said gathering means are generally peripherally disposed about respective said leg openings to provide elasticity thereto and to prevent leakage thereat, and said stretchable side panels provide generally inwardly directed force vectors against a wearer to maintain said garment snugly against the wearer's body both before and after a discharge.

39. The garment of claim 38, wherein an upper end segment portion of at least one of said stretchable side panels tapers inwardly and upwardly toward said waist opening.

40. The garment of claim 39 wherein the length of said end segment portion is about 3% to about 40% of the total length of said garment.

41. The garment of claim 40 wherein the length of said end segment portion is about 5% to about 25% of the total length of said garment.

42. The garment of claim 41 wherein the length of said end segment portion is about 10% to about 15% of the total length of said garment.

43. The garment of claim 39 wherein said end segment portion angles inwardly toward said waist opening between about 5° to about 55°.

44. The garment of claim 43 wherein said end segment portion angles inwardly toward said waist opening between about 10° to about 40°.

45. The garment of claim 44 wherein said end segment portion angles inwardly toward said waist opening between about 15° to about 30°.

46. The garment of claim 38, wherein the front edge portion of each said leg opening is nearer to said waist opening than the back edge portion.

47. The garment of claim 38, wherein each said stretchable side panel is a stretch-bonded laminate comprising a stretchable layer stretch-bonded to a gatherable layer, whereby upon relaxing said stretch-bonded layers, said gatherable layer is gathered.

48. The garment of claim 47 wherein said stretch-bonded laminate comprises a second gatherable layer, said stretchable layer being stretch-bonded to said second gatherable layer, whereby upon relaxing said stretch-bonded layers, said second gatherable layer is gathered.

49. A disposable pant-like garment for absorbing human discharge comprising:
an absorbent assembly comprising a liquid-impervious outer cover, a liquid-pervious liner, and an absorbent medium therebetween; said absorbent assembly further comprising generally opposite side edges and generally opposite end edges,
stretchable side panels being joined to said side edges to form with said absorbent assembly a waist opening and a pair of leg openings, and
a gathering means being joined along a crotch portion of each said leg opening for gathering said crotch portion,
said stretchable side panels bordering a remaining portion of each said leg opening in a relatively non-gathered manner.

50. A disposable pant-like garment for absorbing human discharge comprising:
an absorbent assembly comprising an outer cover and an absorbent medium; said absorbent assembly further comprising generally opposite side edges and generally opposite end edges,
stretchable side panels being joined to said side edges to form with said absorbent assembly a waist opening and a pair of leg openings, and
a gathering means being joined along a crotch portion of each said leg opening for gathering said crotch portion,
said stretchable side panels bordering a remaining portion of each said leg opening in a relatively non-gathered manner.

51. A disposable child's training pant, comprising:
an absorbent assembly comprising an outer cover and an absorbent medium; said absorbent assembly further comprising generally opposite side edges and generally opposite end edges,
stretchable side panels being joined to said side edges to form with said absorbent assembly a waist opening and a pair of leg openings, and
a gathering means being joined along a crotch portion of each said leg opening for gathering said crotch portion,
said stretchable side panels bordering a remaining portion of each said leg opening in a relatively non-gathered manner.

* * * * *

UNITED STATES PATENT AND TRADEMARK OFFICE
CERTIFICATE OF CORRECTION

PATENT NO. : 4,940,464  
DATED : July 10, 1990  
INVENTOR(S) : Paul T. Van Gompel; Jody D. Suprise; Robert J. Schleinz It is certified that error appears in the above-identified patent and that said Letters Patent is hereby corrected as shown below:

Column 12, line 17, delete "40" and substitute therefor --44--.

Claim 2, Column 13, line 24, after the number "1", insert ", 49, 50, or 51".

Claim 5, Column 13, line 34, after "claim 1,", insert "49, 50, or 51".

Claim 8, Column 13, line 40, after "claim 1,", insert "49, 50, or 51".

Claim 9, Column 13, line 42, after "claim 1,", insert "49, 50, or 51".

Claim 10, Column 13, line 45, after "claim 1,", insert "49, 50, or 51".

Claim 12, Column 13, line 51, after "claim 1,", insert "49, 50, or 51".

Claim 13, Column 13, line 55, after "claim 1,", insert "49, 50, or 51".

Claim 14, Column 13, line 58, after "claim 1,", insert "49, 50, or 51"; line 62, delete "sad" and substitute therefor --said--.

Claim 16, Column 14, line 1, delete ", or" and substitute therefor --or 49--.

Claim 17, Column 14, line 4, delete "or" and substitute therefor --49, 50, or 51--.

UNITED STATES PATENT AND TRADEMARK OFFICE
CERTIFICATE OF CORRECTION

PATENT NO. : 4,940,464

DATED : July 10, 1990

INVENTOR(S) : Paul T. Van Gompel; Jody D. Suprise; Robert J. Schleinz

Page 2 of 3

It is certified that error appears in the above-identified patent and that said Letters Patent is hereby corrected as shown below:

(continued from Page 1)

Claim 20, Column 14, line 14, delete "sad" and substitute therefor --said--.

Claim 24, Column 14, line 33, after "claim 1,", insert "49, 50, or 51".

Claim 26, Column 14, line 39, after "claim 1", insert ", 49, 50, or 51".

Claim 27, Column 14, line 42, delete "500%" and substitute therefor --300%--.

Claim 29, Column 14, line 45, after "claim 1,", insert "49, 50, or 51".

Claim 32, Column 14, line 55, after "claim 1,", insert "49, 50, or 51".

Claim 35, Column 14, line 64, after "claim 1,", insert "49, 50, or 51".

Claim 36, Column 15, line 1, after "claim 1,", insert "49, 50, or 51".

Claim 37, Column 15, line 5, delete "member" and substitute therefor --members--.

Claim 38, Column 15, line 27, delete "sad" and substitute therefor --said--.

Claim 39, Column 15, line 37, after "claim 38,", insert "49, 50, or 51".

UNITED STATES PATENT AND TRADEMARK OFFICE
CERTIFICATE OF CORRECTION

PATENT NO. : 4,940,464
DATED : July 10, 1990
INVENTOR(S) : Paul T. Van Gompel; Jody D. Suprise; Robert J. Schleinz It is certified that error appears in the above-identified patent and that said Letters Patent is hereby corrected as shown below:

(continued from Page 2)

Claim 46, Column 16, line 1, after "claim 38,", insert "49, 50, or 51".

Claim 47, Column 16, line 4, after "claim 38,", insert "49, 50, or 51".

Signed and Sealed this

Seventh Day of April, 1992

Attest:

HARRY F. MANBECK, JR.

*Attesting Officer*     *Commissioner of Patents and Trademarks*